United States Patent [19]
Quadbeck-Seeger

[11] 4,083,849
[45] Apr. 11, 1978

[54] PROCESS FOR PREPARATION OF 5-CYANOPYRID-6-ONES

[75] Inventor: Hans-Juergen Quadbeck-Seeger, Bad Durkheim, Germany

[73] Assignee: BASF Aktiengesellschaft, Ludwigshafen am Rhein, Germany

[21] Appl. No.: 698,916

[22] Filed: Jun. 23, 1976

[30] Foreign Application Priority Data

Jul. 11, 1975 Germany .............................. 2531035

[51] Int. Cl.² .......................................... C07D 213/57
[52] U.S. Cl. ................................................. 260/294.9
[58] Field of Search ...................................... 260/294.9

[56] References Cited

U.S. PATENT DOCUMENTS

| 3,487,066 | 12/1969 | Ritter et al. | 260/156 |
| 3,640,674 | 2/1972 | Berrie et al. | 8/41 |
| 3,905,951 | 9/1975 | Berrie et al. | 260/156 |
| 3,923,776 | 12/1975 | Gnad | 260/156 |

Primary Examiner—Alan L. Rotman
Attorney, Agent, or Firm—Keil, Thompson & Shurtleff

[57] ABSTRACT

5-Cyanopyrid-6-ones are manufactured by reacting haloacetic acid esters with nitrogen compounds, then reacting the mixture with alkali metal cyanides, and finally reacting it with dicarbonyl compounds. The products are starting materials for the manufacture of dyes, assistants, pharmaceuticals, vitamin B 6, crop protection agents and aminoacids.

8 Claims, No Drawings

PROCESS FOR PREPARATION OF 5-CYANOPYRID-6-ONES

The present invention relates to a process for the manufacture of 5-cyanopyrid-6-ones by reacting haloacetic acid esters with nitrogen compounds, then reacting the mixture with alkali metal cyanides and finally reacting it with dicarbonyl compounds.

J. Org. Chem., 25 (1960), 560–564, discloses that the condensation of ethyl acetoacetate with cyanoacetamide in the presence of piperidine or potassium hydroxide gives 3-cyano-2,6-dihydroxy-4-methylpyridine; it is assumed that the particular method used, namely isolating the piperidinium salt or potassium salt formed as an intermediate, dissolving the isolated salt and acidifying the solution, is responsible for the good yields of 3-cyano-2,6-dihydroxy-4-methylpyridine.

Cyanoacetamide has hitherto been manufactured almost exclusively by reaction of cyanoacetic acid esters with aqueous ammonia (Org. Synth., Coll. vol I, 179 (1956), and Houben-Weyl, Methoden der Organischen Chemie, volume 8, (1952), 658). The synthesis of 3-cyano-2,6-dihydroxy-4-methylpyridine or cyanoacetamide therefore requires starting from cyanoacetic acid esters, the manufacture of which is known to present a number of problems. If alkyl chloroacetates are used as starting materials, as disclosed, e.g., in German Pat. No. 640,509, and are reacted with alkali metal cyanides at an elevated temperature in the presence of a free organic acid, the formation of by-products cannot be suppressed. In spite of using mild conditions, the by-products include, inter alia, cyanosuccinic acid esters and other condensation products of the cyanoacetic acid ester produced, which are formed especially under alkaline and neutral conditions. Though, in the above patent, the reaction is discontinued after only about 60 percent conversion, the yield remains unsatisfactory. In order to suppress objectionable side reactions of the cyanoacetic acid ester formed in the reaction mixture, German Pat. No. 1,210,789 proposes carrying out the reaction with an excess of hydrocyanic acid, in the presence of alkali metal alcoholates. However, complete conversion is not achievable even by this method. In addition, the use of fluid hydrocyanic acid, and the isolation of its excess, require extensive safety precautions on an industrial scale.

Japanese Patent Publication No. 17,886/1967 discloses that chloroacetic acid amides can be reacted with alkali metal cyanides, in acetonitrile as the solvent, to give cyanoacetamide. It is pointed out that by using acetonitrile as the solvent, hydrolysis of the end product is avoided. For working up, the reaction mixture must first be treated with hydrochloric acid to decompose unconverted sodium cyanide, sodium chloride formed must then be filtered off, and finally the acetonitrile must be distilled off.

It is an object of the present invention to provide a new process whereby 5-cyanopyrid-6-ones can be manufactured more simply and more economically, with a better space-time yield and in higher purity.

I have found that this object is achieved and that 5-cyanopyrid-6-ones of the formula

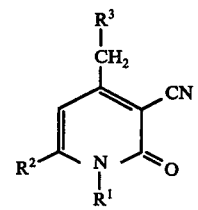

where $R^1$, $R^2$ and $R^3$ may be identical or different and each is an aliphatic radical, and in addition $R^1$ may be hydrogen or a cycloaliphatic radical, $R^2$ may be hydroxyl and/or $R^3$ may be hydrogen or alkoxy are obtained in an advantageous manner by reaction of dicarbonyl compounds with cyanoacetamides if, in a first step, a haloacetic acid ester of the formula

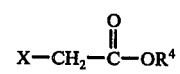

where $R^4$ is an aliphatic or cycloaliphatic radical and X is halogen, is reacted with a nitrogen compound of the formula

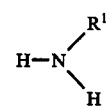

where $R^1$ has the above meanings, the haloacetamide thus obtained, of the formula

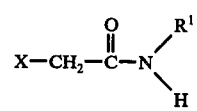

where $R^1$ and X have the above meanings, is then reacted, in a second step, in situ, with an alkali metal cyanide or alkaline earth metal cyanide, and thereafter, in a third step, the cyanoacetamide thus obtained, of the formula

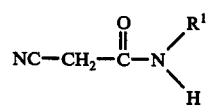

where $R^1$ has the above meanings, is reacted, in situ, with a dicarbonyl compound of the formula

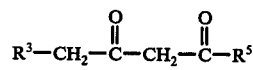

where $R^3$ has the above meanings and $R^5$ represents an aliphatic radical or alkoxy, in the presence of a basic compound, after which the reaction mixture is acidified.

Further, I have found that the process may be carried out advantageously if, in a first step, a haloacetic acid of the formula

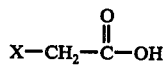

where X has the above meaning, is reacted with an alkanol of the formula $$R^4—OH \qquad \text{VIII}$$

where $R^4$ has the above meanings, and the haloacetic acid ester II thus formed is then reacted, in situ, by the 3 steps mentioned above, to give the 5-cyanopyrid-6-ones, after which the reaction mixture is acidified.

Where chloroacetic acid or methyl chloroacetate, ammonia, sodium cyanide and methyl acetoacetate are used, the reaction may be represented by the following equations:

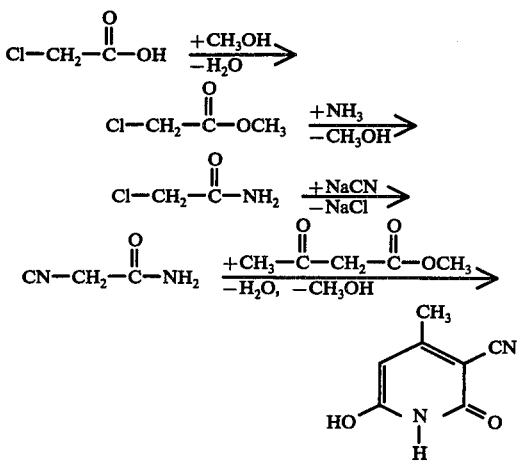

Compared to the conventional processes, the process of the invention gives 5-cyanopyrid-6-ones more simply and more economically, in better space-time yield and higher purity. It is particularly advantageous, especially for industrial operation, that the end product I can be manufactured by a three- or four-stage method, which, however, is carried out in one and the same vessel, from a haloacetic acid ester or a haloacetic acid, without isolation the intermediates IV, V and, if the acid is used as the starting material, also II. Since working up of reaction mixtures and the preparation of starting mixtures for subsequent stages is made unnecessary, the process of the invention is also more reliable in operation, causes less pollution of the environment, and saves costs. By-products are not formed to a significant degree. All these advantageous results are surprising, particularly in view of the publications cited above, since substantial hydrolysis of the starting material and intermediates, the formation of numerous by-products, and a substantially lower yield of end product would have been expected.

The starting materials II are reacted with the starting materials III in stoichiometric amount or in excess, preferably in a ratio from 1 to 4 moles of starting material III per mole of starting material II. Preferred starting materials II, and other materials III, IV, V, VI, VII, VIII and, accordingly, preferred end products I are those where $R^1$, $R^2$ and $R^3$ are identical or different and each is alkyl of 1 to 7 carbon atoms, but $R^1$ may also be hydrogen, $R^2$ may be hydroxyl and/or $R^3$ may be hydrogen, cyclohexyl or alkoxy of 1 to 7 carbon atoms, $R^4$ is alkyl of 1 to 7 carbon atoms or cyclohexyl, X is bromine and especially chlorine, and $R^5$ is alkyl or alkoxy each of 1 to 7 carbon atoms. The above radicals may in addition be substituted by groups which are inert under the reaction conditions, e.g., cyano, or alkyl or alkoxy each of 1 to 4 carbon atoms.

Thus, e.g., the following haloacetic acid esters may be used as starting materials II: methyl, ethyl, n-propyl, isopropyl, n-butyl, isobutyl, sec.-butyl, tert.-butyl, pentyl, pent-2-yl, pent-3-yl, n-hexyl, cyclohexyl, n-heptyl, n-octyl, n-nonyl, n-decyl, 2-ethylhexyl, 2,2,6-trimethyl-n-heptyl, 2-ethylpentyl, 3-ethylpentyl, 2,3-dimethyl-n-butyl, 2,2-dimethyl-n-butyl, 2-methylpentyl, 3-methylpentyl, 2,2,4-trimethylheptyl, 2-methylheptyl, 3-methylheptyl, 4-methylheptyl, 3-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 2-methyl-3-ethylpentyl, 3-methyl-3-ethylpentyl, 2,2,3-trimethylpentyl, 2,2,4-trimethylpentyl, 2,3,3-trimethylpentyl, 2,3,4-trimethylpentyl and 2,2,3,3-tetramethylbutyl bromoacetate and, especially, chloroacetate. The methyl, ethyl, n-propyl, isopropyl, n-butyl, isobutyl, sec.-butyl and tert.-butyl esters, and especially the methyl and ethyl esters, and particularly preferred.

Accordingly, the alkanols of the above esters, advantageously of the preferred esters, and especially methanol or ethanol, can be used as starting materials VIII, and chloroacetic acid and bromoacetic acid can be used as starting materials VII.

Examples of suitable starting materials III are: pentylamine, pent-2-ylamine, pent-3-ylamine, n-hexylamine, cyclohexylamine, n-heptylamine, n-octylamine, n-nonylamine, n-decylamine, 2-ethylhexylamine, 2,2,6-trimethyl-n-heptylamine, 2-ethylpentylamine, 3-ethylpentylamine, 2,3-dimethyl-n-butylamine, 2,2-dimethyl-n-butylamine, 2-methylpentylamine, 3-methylpentylamine, 2,2,4-trimethylheptylamine, 2-methylheptylamine, 3-methylheptylamine, 4-methylheptylamine, 3-ethylhexylamine, 2,2-dimethylhexylamine, 2,3-dimethylhexylamine, 2,4-dimethylhexylamine, 2,5-dimethylhexylamine, 3,3-dimethylhexylamine, 3,4-dimethylhexylamine, 2-methyl-3-ethylpentylamine, 3-methyl-3-ethylpentylamine, 2,2,3-trimethylpentylamine, 2,2,4-trimethylpentylamine, 2,3,3-trimethylpentylamine, 2,3,4-trimethylpentylamine and 2,2,3,3-tetramethylbutylamine; methylamine, ethylamine, n-propylamine, isopropylamine, n-butylamine, isobutylamine, sec.-butylamine, tert.-butylamine and ammonia are preferred.

The first step of the process, namely the reaction of the starting materials II and III, is in general carried out at from −5° C to 150° C, preferably from 0° to 60° C, under reduced pressure, superatmospheric pressure or, preferably, atmospheric pressure, and batchwise or continuously. It can be carried out in the absence or in the presence of solvents, advantageously of water. The water is preferably added in the form of appropriate ammonia solutions or amine solutions. Advantageously, the amount of water used is such that the starting mixture is dissolved as completely as possible. Preferably, a total, for all 3 steps, of from 0 to 10,000, especially from 10 to 500, percent by weight of water, based on starting material II, is used. If appropriate, alkanols, especially those used for the manufacture of the esters II, and cycloalkanols, e.g., ethanol, n-butanol, isobutanol, methylglycol, tert.-butanol, cyclohexanol, propanol, methanol, 2-ethylhexanol, nonyl alcohol and dodecyl alcohol, ethers, e.g., ethyl propyl ether, diisobutyl ether, methyl tert.-butyl ether, n-butyl ethyl ether, di-n-butyl ether, dioxane, di-iso-amyl ether, diisopropyl ether, anisole, phenetole, cyclohexyl methyl ether, diethyl ether, tetrahydrofuran, thioanisole and β,β′- dichlorodiethyl ether, ketones, such as methyl ethyl ketone, diethyl ketone, acetophenone and cyclohexanone, acid amides, such as N,N-dimethylbenzamide, N,N-dimethylformamide, N,N-dimethylacetamide, N,N-dimethylphenylacetamide, N,N-dimethylcyclohexanecarboxylic acid amide, N,N-dimethylpropionamide, the homologous carboxylic acid piperidide and carboxylic acid pyrrolidide, and corresponding N,N-diethyl-, N,N-diisopropyl-, N,N-dibenzyl-, N,N-diphenyl-, N-methyl-N-phenyl-, N-cyclohexyl-N-methyl- and N-ethyl-N-tert.-butylcompounds, or appropriate mixtures of the above, may be added as organic solvents. The organic solvent is advantageously used in a total amount, for all 3 steps, of from 50 to 3,000 percent by weight, preferably from 100 to 1,000 percent by weight, based on starting material II.

The second of the reaction is carried out after addition of cyanides, advantageously together with the above solvents, especially water, to the reaction mixture from the first step, which contains the haloacetamide IV which has been formed. The second step is in general carried out at from $-5°$ to $150°$ C, preferably from $10°$ to $100°$ C, under reduced pressure, superatmospheric pressure or, preferably, atmospheric pressure, and batchwise or continuously. The starting material II or IV can be reacted with the cyanide in stoichiometric amount or in excess, preferably in a ratio of from 1 to 4 equivalents of cyanide per mole of starting material II. Alkaline earth metal cyanides, e.g., magnesium cyanide and calcium cyanide or, preferably, alkali metal cyanides, such as lithium cyanide and potassium cyanide and, advantageously, sodium cyanide, are used.

The third step of the reaction is carried out after adding dicarbonyl compounds VI and a basic compound to the reaction mixture from the second step, which contains the cyanoacetamide V which has been formed. It is advantageous also to add one of the above solvents, advantageously water in the form of a solution of the basic compound. The starting material VI can be reacted with the starting material V or II in stoichiometric amount or in excess, preferably using a ratio of from 1 to 4 moles of starting material VI per mole of starting material II. In general, the third step is carried out at from $10°$ to $180°$ C, preferably from $30°$ to $120°$ C, under reduced pressure, superatmospheric pressure or, preferably, atmospheric pressure, and batchwise or continuously. The materials V and VI are reacted with a basic compound in an amount of less than 1.5 times, preferably from 0.6 to 1.4 times, and especially from 0.9 to 1.1 times, the equivalent weight, based on starting material II. Preferred basic compounds are primary, secondary and especially tertiary amines, alkaline earth metal compounds, ammonium compounds and, especially, alkali metal compounds and ammonia, and appropriate mixtures. Alkali metal compounds, ammonium compounds and alkaline earth metal compounds which can be used advantageously are the hydroxides, oxides, carbonates, bicarbonates, salts or weak and/or polybasic acids, and alcoholates of calcium, barium and lithium and especially of sodium and potassium. Examples of such basic compounds are potassium hydroxide, sodium hydroxide, potassium carbonate, sodium carbonate, lithium carbonate, sodium bicarbonate, potassium bicarbonate, calcium hydroxide, barium oxide, calcium carbonate, sodium acetate, sodium propionate, sodium ethyleneglycolate, sodium methylate, sodium ethylate, sodium tripropylene-glycolate, trimethylamine, triethylamine, pyridine, diethylaniline, dimethylaminoethanol, N-ethylpiperidine, N-methylpyrrolidine, ethylamine, diethylamine, aniline, N-methylaniline, benzylamine, cyclohexylamine, di-tert.-butylamine and isopropylamine, but ammonia is preferred.

Suitable starting materials VI are the pentyl, pent-2-yl, pent-3-yl, n-hexyl, n-heptyl, n-octyl, N-nonyl, n-decyl, 2-ethylhexyl, 2,2,6-trimethyl-n-heptyl, 2-ethylpentyl, 3-ethylpentyl, 2,3-dimethyl-n-butyl, 2,2-dimethyl-n-butyl, 2-methylpentyl, 3-methylpentyl, 2,2,4-trimethylheptyl, 2-methylheptyl, 3-methylheptyl, 4-methylheptyl, 3-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 2-methyl-3-ethylpentyl, 3-methyl-3-ethylpentyl, 2,2,3-trimethylpentyl, 2,2,4-trimethylpentyl, 2,3,3-trimethylpentyl, 2,3,4-trimethylpentyl and 2,2,3,3-tetramethylbutyl esters, and especially the methyl, ethyl, n-propyl, isopropyl, n-butyl, isobutyl, sec.-butyl and tert.-butyl esters of acetoacetic acid as well as of methyl-, ethyl-, n-propyl-, isopropyl-, n-butyl-, isobutyl-, sec.-butyl- and tert.-butyl-($\omega$)-acetoacetic acid, di-(methyl)-, di-(ethyl)-, di-(n-propyl)-, di-(isopropyl)-, di-(n-butyl)-, di-(isobutyl)-, di-(sec.-butyl)- and di-(tert.-butyl)-($\omega,\omega'$)-acetylacetone, and acetylacetone itself, and the methyl, ethyl, n-propyl, isopropyl, n-butyl, isobutyl, sec.-butyl and tert.-butyl ethers of $\gamma$-hydroxyacetoacetic acid (which are esterified like the above acetoacetic acid esters), and of 5-hydroxyacetylacetone.

The reaction may be carried out as follows: a mixture of the starting material II and the starting material III, if appropriate together with water and solvent, is kept at the reaction temperature for from 0.5 to 4 hours. The cyanide, advantageously together with solvent, is then added, and in the 2nd step the mixture is kept at the reaction temperature for from 1 to 6 hours. The starting material VI and the basic compound, if appropriate together with solvent, are then added and the 3rd step is carried out at the reaction temperature for from 1 to 6 hours. The above total amounts of water and/or organic solvent can be added completely from the start, i.e., when carrying out the first step, but are advantageously added only partly — especially as far as the water is concerned — at that stage, with the remaining proportions, especially of water, being added during the second step or the second and third steps. At the end of the third step, e.g., when using ammonia as the basic compound, the end product I frequently precipitates directly in the form of its ammonium salt. The reaction mixture is next acidified, in general, to a pH of from 0 to 3, preferably from 0.5 to 2.

Inorganic acids, in particular, may be used for acidifying the mixture. Instead of monobasic acids, equivalent amounts of polybasic acids may be used. The following acids are preferred: hydrogen chloride, hydrogen bromide, sulfuric acid, phosphoric acid and nitric acid. The acids may be added in concentrated form, as mixtures with one another, and/or as mixtures with a solvent, especially one of those mentioned above.

Thereafter, the end product is isolated from the reaction mixture by conventional methods, e.g., by filtration.

In a preferred embodiment, the preparation of the starting material II from a haloacetic acid VII and an alkanol VIII, and the reaction according to the invention, are carried out in two stages in one and the same vessel. The acid is advantageously bromoacetic acid and especially chloroacetic acid. The starting material VII can be reacted with the starting material VIII in stoichiometric amount or in excess, preferably in a ratio of from 1 to 10 moles of starting material VIII per mole of starting material VII. In general, the reaction is carried out at from 30° to 150° C, preferably from 50° to 110° C, under atmospheric or superatmospheric pressure, and continuously or batchwise. Advantageously, no solvent is added and the mixture of the starting materials, or the starting material VIII, is used as the reaction medium; however, where appropriate the solvents mentioned above, in the amount mentioned, may be used as the medium. The reaction is in general carried out in the presence of an acid, e.g., one of the above acids, advantageously phosphoric acid, a sulfonic acid or, in particular, hydrogen chloride and sulfuric acid; amounts of from 0.5 to 15, especially from 3 to 10, percent by weight of acid, based on starting material VII, may be used.

The reaction can be carried out as follows: a mixture of the starting materials VII and VIII, acid and, if appropriate, solvent is kept at the reaction temperature for from 1 to 12 hours. The starting material III and, if appropriate, a solvent are then added to the reaction mixture and the process according to the invention is carried out in three steps in the above manner.

The 5-cyanopyrid-6-ones which may be manufactured by the process of the invention are valuable starting materials for the manufacture of dyes, assistants, pharmaceuticals, vitamin B 6, crop protection agents and aminoacids. They may also be used as couplers for azo dyes. Their use is described in the publications mentioned earlier, in British Pat. No. 1,095,829 and in W. H. Sebrell and R. S. Harris, The Vitamins, volume II, pages 8-117 (Second Ed., Academic Press, N.Y. 1968).

In the Examples which follow, parts are by weight.

EXAMPLE 1

80.5 Parts of an aqueous ammonia solution (21.2 percent strength by weight) are added to 109 parts of methyl chloroacetate at from 0° to 15° C. The reaction mixture is stirred for 1 hour at 10° to 15° C. 167 Parts of a 29.4 percent strength by weight sodium cyanide solution and 125 parts of water are then added and the reaction mixture is stirred for 5 hours at 40° C. After adding 116 parts of methyl acetoacetate, the mixture is rendered alkaline with 121 parts of a 21.2 percent strength aqueous ammonia solution. It is then stirred for 3 hours at 90° C, 350 parts of water are added, the batch is acidified to pH 2 with concentrated hydrochloric acid and is filtered, and the filtered residue is washed. The yield is 90 parts of 2-hydroxy-5-cyano-4-methylpyrid-6-one (60% of theory, based on methyl chloroacetate employed) of melting point 303°-306° C (with decomposition).

EXAMPLE 2

92 Parts of an 18.5 percent strength by weight aqueous solution of ammonia are added to 122.5 parts of ethyl chloroacetate at from 10° to 15° C. After stirring for 2 hours, 200 parts of dimethylformamide and 167 parts of a 29.4 percent strength by weight solution of sodium cyanide in water are added. The reaction mixture is kept for 3 hours at 40° C, and 130 parts of ethyl acetoacetate are then added, followed by 139 parts of an 18.5 percent strength by weight aqueous ammonia solution. The mixtue is kept for 4 hours at 90° to 95° C. It is then worked up as described in Example 1. 10.2 parts of 2-hydroxy-5-cyano-4-methylpyrid-6-one (68% of theory, based on ethyl chloroacetate employed) of melting point 298°-302° C (with decomposition) are obtained.

EXAMPLE 3

78 Parts of a 40 percent strength by weight aqueous methylamine solution are added to 109 parts of methyl chloroacetate at from 10° to 15° C. Afer stirring for a further hour, 125 parts of water and 167 parts of a 29.4 percent strength by weight sodium cyanide solution are added. The mixture is kept for 4 hours at 40° C, 116 parts of methyl acetoacetate and 123 parts of a 20.8 percent strength by weight aqueous ammonia solution are then added and the batch is kept at 90° C for 4 hours. It is then worked up as described in Example 1, 103 parts of 1,4-dimethyl-2-hydroxy-5-cyanopyrid-6-one (63% of theory, based on methyl chloroacetate employed) of melting point 279°-281° C are obtained.

EXAMPLE 4

122.5 Parts of ethyl chloroacetate are added, at from 10° to 15° C, to 90 parts of a 50 percent strength by weight solution of ethylamine in water. After a reaction time of 2 hours, 225 parts of water and 65 parts of solid potassium cyanide are added. The mixture is kept at 40° C for 5 hours, and 116 parts of methyl acetoacetate and 120 parts of 21.5 percent strength by weight aqueous ammonia solution are then added. The batch is stirred for 6 hours at 90° C and is worked up as described in Example 1. 107 parts of 1-ethyl-2-hydroxy-5-cyano-4-methylpyrid-6-one (60% of theory, based on ethyl chloroacetate) of melting point 230°-237° C are obtained.

EXAMPLE 5

73 Parts of n-butylamine are added to 109 1 parts of methyl chloroacetate at from 10° to 15° C. The reaction mixture is stirred for a further 2 hours at 15° C and 125 parts of dimethylformamide and 167 parts of a 30 percent strength by weight aqueous sodium cyanide solution are then added. The mixture is stirred for 5 hours at 40° C. After adding 116 1 parts of methyl acetoacetate and 123 parts of a 21 percent strength by weight aqueous ammonia solution, the mixture is stirred for 4 hours at 90° C and is worked up as described in Example 1. 120 parts of 1-butyl-2-hydroxy-5-cyano-4-methylpyrid-6-one (58% of theory, based on methyl chloroacetate) of melting point 218°-222° C are obtained.

I claim:

1. A process for the preparation of 5-cyanopyrid-6-ones of the formula $$\underset{R^1}{\underset{|}{\underset{\substack{\\}}{}}}\text{(I)}$$

where $R^1$ and $R^3$ are identical or different and each is alkyl of 1 to 7 carbon atoms, $R^1$ may also be hydrogen, $R^2$ is hydroxyl and $R^3$ may also be hydrogen, cyclohexyl, or alkoxy of 1 to 7 carbon atoms, wherein, in a first step, a haloacetic acid ester of the formula

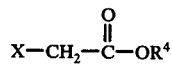

where $R^4$ is alkyl of 1 to 7 carbon atoms and X is bromine or chlorine, is reacted with a nitrogen compound of the formula

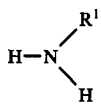

where $R^1$ has the above meanings, the haloacetamide thus obtained of the formula

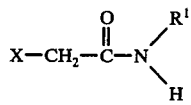

where $R^1$ and X have the above meanings, is then reacted, in a second step, in situ, with an alkali metal cyanide or alkaline earth metal cyanide, and thereafter, in a third step, the cyanoacetamide thus obtained, of the formula

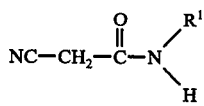

where $R^1$ has the above meanings, is reacted, in situ, with a dicarbonyl compound of the formula

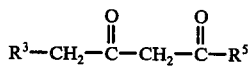

where $R^3$ has the above meanings and $R^5$ represents alkoxy of 1 to 7 carbon atoms, in the presence of a basic compound, after which the reaction mixture is acidified.

2. A process as claimed in claim 1, wherein a first step, a haloacetic acid of the formula

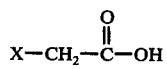

where X has the above meaning, is reacted with an alkanol of the formula

where $R^4$ has the above meaning, and the haloacetic acid ester II thus formed is then reacted, in situ, by the 3 steps mentioned above, to give the 5-cyanopyrid-6-ones, after which the reaction mixture is acidified.

3. A process as claimed in claim 1, wherein the reaction is carried out using a ratio of from 1 to 4 moles of starting material III per mole of starting material II.

4. A process as claimed in claim 1, wherein the reaction is carried out in the presence of from 0 to 10,000 percent by weight of water, based on starting material II, or in the presence of from 50 to 3,000 percent by weight of an organic solvent, based on starting material II.

5. A process as claimed in claim 1, wherein the reaction of the starting materials II and III is carried out at from $-5°$ to $150°$ C, the second step is carried out at from $-5°$ to $150°$ C and the third step is carried out at from $10°$ to $180°$ C.

6. A process as claimed in claim 1, wherein the reaction is carried out using a ratio of from 1 to 4 equivalents of cyanide per mole of starting material II.

7. A process as claimed in claim 1, wherein the reaction is carried out using a ratio of from 1 to 4 moles of starting material VI per mole of starting material II.

8. A process as claimed in claim 1, wherein the reaction of the compounds V and VI is carried out with a basic compound used in an amount of from 0.6 to 1.4 equivalents, based on starting material II.

* * * * *

UNITED STATES PATENT AND TRADEMARK OFFICE
CERTIFICATE OF CORRECTION

PATENT NO. : 4,083,849
DATED : April 11, 1978
INVENTOR(S) : Hans-Juergen Quadbeck-Seeger It is certified that error appears in the above-identified patent and that said Letters Patent are hereby corrected as shown below:

Column 10, line 4, after "wherein" insert --in--.

Signed and Sealed this

Fifteenth Day of August 1978

[SEAL]

Attest:

RUTH C. MASON
Attesting Officer

DONALD W. BANNER
Commissioner of Patents and Trademarks